United States Patent [19]

Hall

[11] Patent Number: 4,804,846
[45] Date of Patent: Feb. 14, 1989

[54] PHOTOIONIZATION DETECTOR FOR GAS CHROMATOGRAPHY

[75] Inventor: Randall C. Hall, College Station, Tex.

[73] Assignee: O. I. Corporation, College Station, Tex.

[21] Appl. No.: 128,644

[22] Filed: Dec. 4, 1987

[51] Int. Cl.$^4$ .................... H01J 27/24; G01N 21/00
[52] U.S. Cl. .................... 250/379; 250/288; 250/382; 250/423 P; 250/432 R; 324/465
[58] Field of Search .............. 250/423 P, 435, 432 R, 250/382, 379, 288 A, 288; 324/464, 465

[56] References Cited

U.S. PATENT DOCUMENTS

| | | | |
|---|---|---|---|
| 3,933,432 | 1/1976 | Driscoll | 436/100 |
| 4,013,913 | 3/1977 | Driscoll et al. | 313/242 |
| 4,028,617 | 6/1977 | Kamo et al. | 324/464 |
| 4,063,156 | 12/1977 | Patterson | 324/465 |

FOREIGN PATENT DOCUMENTS

| | | | |
|---|---|---|---|
| 248880 | 8/1987 | German Democratic Rep. | 250/423 P |
| 960617 | 9/1982 | U.S.S.R. | 324/464 |
| 1173292 | 8/1985 | U.S.S.R. | 324/464 |

OTHER PUBLICATIONS

Lovelock, J. E., "Ionization Methods for the Analysis of Gases and Vapors," *Analytical Chemistry*, vol. 33, No. 2, pp. 162-178 (Feb. 1961).

Patterson, P. L., "A Comparison of Different Methods of Ionizing GC Effluents," *Journal of Chromatographic Science*, vol. 24, pp. 466-472 (Nov. 1986).

Driscoll, J. N., and Staziana, F. F., "PID Development Gives New Performance Levels," Reprinted from *Research/Development*, vol. 27, No. 5, pp. 50-52 and 54 (May 1976).

Lovelock, J. E., "A Protoionization Detector for Gases and Vapors," *Nature*, vol. 188, No. 474a, p. 401 (Oct. 29, 1960).

Primary Examiner—Janice A. Howell
Assistant Examiner—Constantine Hannaher
Attorney, Agent, or Firm—Richards, Harris, Medlock & Andrews

[57] ABSTRACT

An improved photoionization detector has a sweep gas inlet which is used to introduce sweep gas near the window of the detector's ultraviolet lamp. The detector's chamber has a vent which allows selective removal of spurious analyte. The detector is adapted to have directly mounted on it, a second detector. Sweep gas used to keep analyte away from the window may be used as a reagent in the second detector. In addition, a means for regulating the ionization lamp voltage is disclosed which prolongs lamp life expectancy.

24 Claims, 3 Drawing Sheets

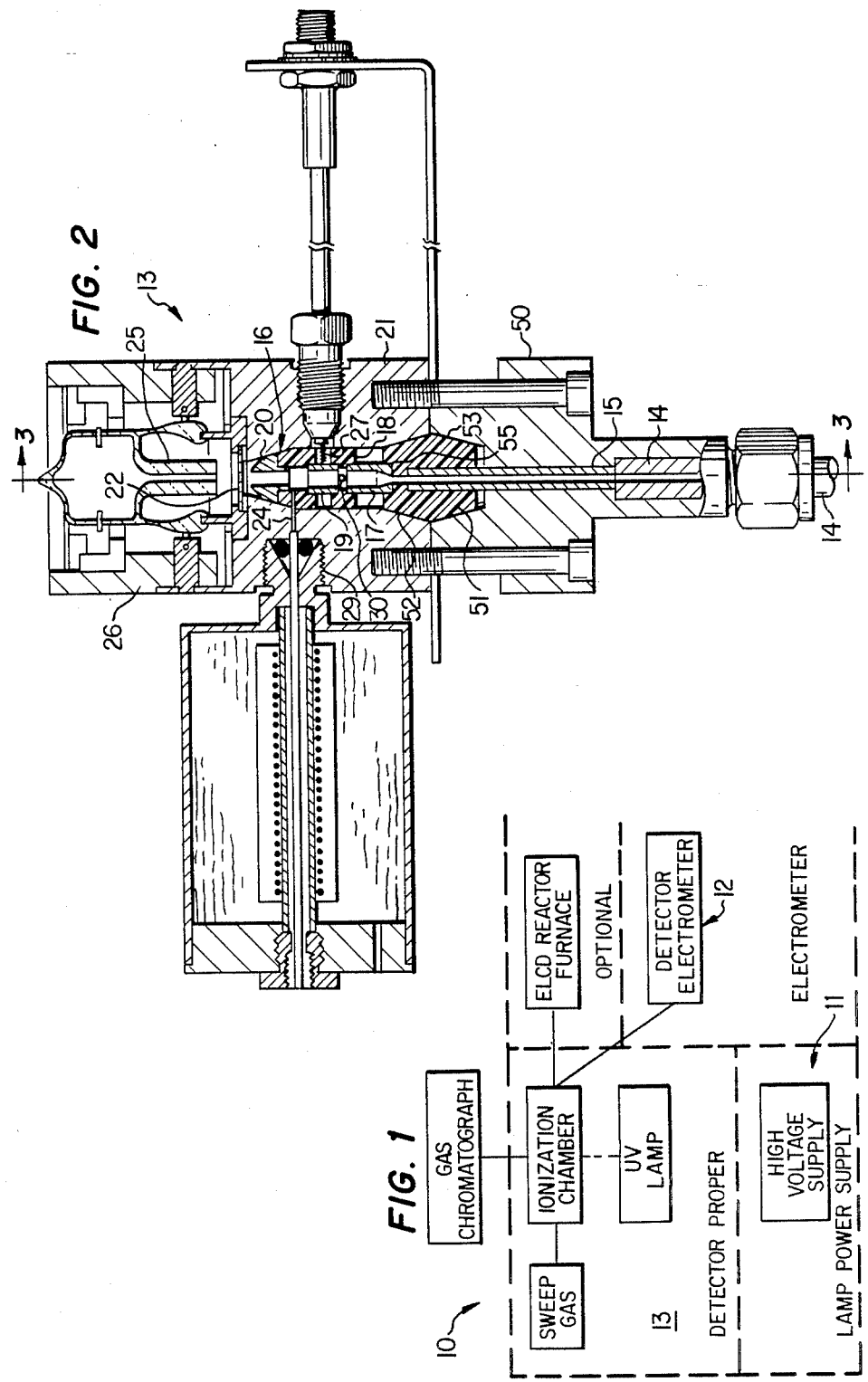

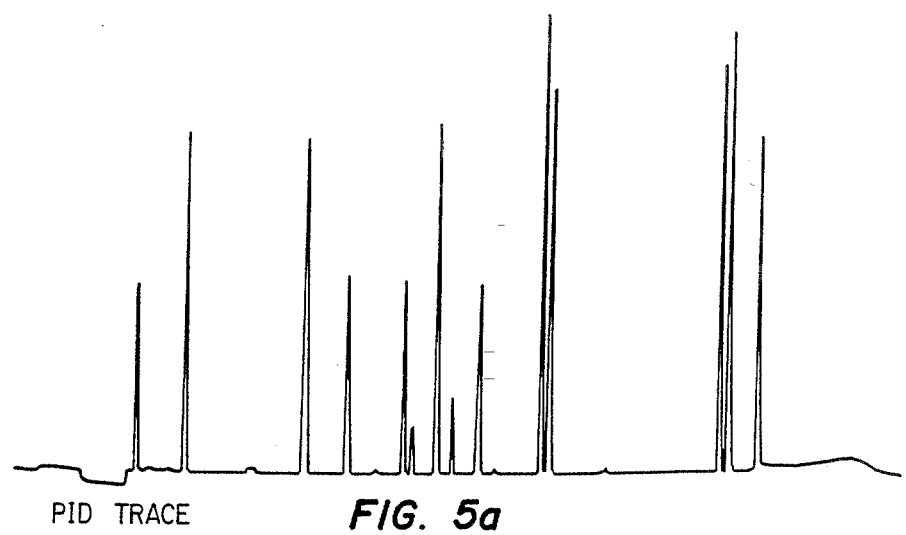
PID TRACE　　　FIG. 5a
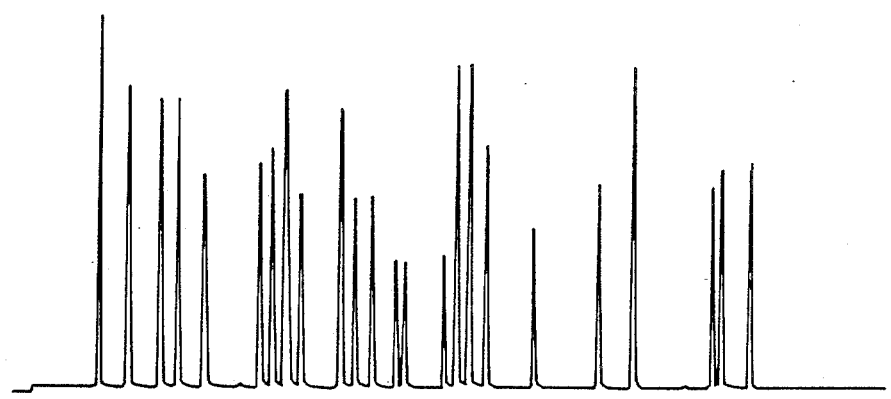
ELCD TRACE　　　FIG. 5b

PHOTOIONIZATION DETECTOR FOR GAS CHROMATOGRAPHY

FIELD OF THE INVENTION

The present invention pertains to photoionization detectors useful in the field of gas chromatography.

BACKGROUND OF THE INVENTION

The use of high energy photoionization for the detection of gas chromatograph (GC) eluates was first reported by J. E. Lovelock in Nature, Volume 188, Page 401, 1960. A variety of ionization techniques have been reviewed and compared also by Lovelock in Analytical Chemistry, Volume 33, page 163, 1961. The photoionization detector (PID) was first commercialized by J. N. Driscoll and F. F. Spaziani of HNU Systems, Inc., who have reviewed the development of the PID in Research/Development, Volume 27, Page 50, 1976. Recently, various ionization techniques used in gas chromatograph detectors have been reviewed by P. L. Patterson in the Journal of Chromatographic Science, Volume 24, Page 466, 1986.

A special electrode arrangement for ion detection within a PID is the subject of U.S. Pat. No. 4,013,913, awarded to Driscoll and Spaziani. An electrode arrangement is disclosed in this patent where an anode and cathode are positioned, with respect to the ionizing radiation, such that an annular configuration is defined with the anode directly exposed to the radiant energy and the cathode shielded from the energy source by either a metallic or an organic plastic material. Such an arrangement is said to produce low noise by minimizing the creation of unwanted photoelectrons from UV radiation striking the cathode.

A PID usually includes a radiant energy source (usually high energy UV light of approximately 10 electron volts), an ionization chamber containing ion accelerator and collecting electrodes, and electronic circuitry for driving the photon source, amplifying the ion current and driving an output device. The sample to be detected is passed as a gas through the ionization chamber where it is exposed to the radiant energy and ionized. The ions formed are accelerated and collected by the electrode structures within the ionization chamber.

Early PIDs had the ionization chamber pneumatically interconnected to the light source which consisted of an emission chamber driven by either a d.c. or r.f. discharge. Sealed light sources were later developed which did not have to be operated under vacuum, did not require the use of ultra-high purity gases and were not susceptible to a change in emission characteristics due to contamination of the discharge electrodes. These sources enabled reliable PIDs to be developed and allowed the PID to be commercialized.

There are two primary problems related to present PID designs. First, the UV lamp window is in contact with the sample stream. Although this is desirable to minimize any unswept volume (dead volume), it allows the window to become fogged by nonvolatile components in the sample stream and by polymer products formed when certain GC eluates such as glycols are irradiated by the UV light. Such window coatings reduce the amount of light reaching the sample and cause a corresponding decrease in detector sensitivity. Detector performance will eventually deteriorate below that which is acceptable and then the lamp, which is quite expensive, must be replaced or the window cleaned if possible.

It is important to minimize dead volume since it causes distortion of the gas chromatograph eluate profiles, which decreases the usefulness of the chromatographic system. Consequently, a PID design which prevents the sample stream from contacting the lamp window without the creation of any dead volume would be an obvious advance in PID technology.

The second problem with present PID designs is the limitations that arise when a PID is connected in series with another detector such as an electrolytic conductivity detector (ELCD). In certain analyses it is analytically advantageous to connect the PID and ELCD so that the sample stream first passes through the PID and then through the ELCD. In this manner such sample components as aromatics and halogenated organics can be analyzed simultaneously with the PID and the ELCD, respectively. This enables all of the compounds of interest in such procedures as EPA methods 502.2, 601 and 602 to be analyzed using a single gas chromatographic run. It should be noted that recent EPA method 502.2 actually requires the use of a PID and an ELCD connected in series.

Several present PID designs that are commercially available have adaptations which enable them to be serially interfaced to another detector, however, they are not truly engineered to be interfaced to the ELCD or any other detector. In the past, serially interfacing the PID and ELCD required the detectors to be mounted in their normal respective manners with a transfer tube connected from the PID exit port to the ELCD inlet port. The PID exit port was normally on the outside of the PID detector body and external to the GC oven, whereas the ELCD inlet was within the GC oven. Thus the transfer tube had to be heated and routed back into the oven to be connected to the ELCD inlet. This was usually done by routing the tube through the hole through which the PID detector inlet port protrudes into the GC oven or another drilled hole. This approach works, but suffers from the following limitations: (a) The transfer tube required to interface the PID to the ELCD is a potential source of leaks due to connections and breakage of the transfer tube (if the recommended, but fragile, materials such as fused silica are used); (b) Sensitive materials can be decomposed by any reactive surfaces of the transfer tube; (c) The integrity of the peak elution profiles can be deteriorated by cold spots and unswept volume in the transfer tube and fittings; and (d) Both detector ports of 2-port chromatographs are required for mounting the PID and ELCD detectors, precluding the use of a third detector.

OBJECTS AND SUMMARY OF THE INVENTION

It is an object of the present invention to provide an improved photoionization detector which is adapted to the analysis of samples containing components of low volatility or components that can polymerize.

It is another object of the present invention to provide an improved photoionization detector which is adapted to be connected serially with another detector such as an ELCD.

It is yet another object of the present invention to provide an improved photoionization detector which is adapted to extend the lifetime of the UV lamp associated with the detector.

It is a further object of the present invention to provide a detector chamber which may be vented.

It is an additional object of the present invention to provide an automatic electronic control to the ionizing lamp which regulates power to the lamp for the purpose of extending lamp life.

These and other objects are met by providing a photoionization detector having a sweep gas inlet port adjacent the window to the radiation source, a vent, the detector adapted to receive a second detector mounted on its exterior without the need for lengthy, interconnection transfer tubes, and further comprising an automatic electronic control of the ionizing lamp.

BRIEF DESCRIPTION OF THE FIGURES

FIG. 1 is a schematic diagram of a system for gas chromatography utilizing the features of the present invention.

FIG. 2 is a cross-sectional view of the photoionization detector of the present invention.

FIGS. 5(a) and 5(b) are representations of detector performance, wherein the features of the present invention are utilized.

DESCRIPTION OF THE INVENTION

A block diagram of the photoionization detector of the present invention is shown in FIG. 1. As can be seen by the dashed line divisions in this figure, the PID 10 consists of three main assemblies—the lamp power supply 11, an electrometer 12 and the detector proper (hereafter referred to as detector 13). As in the design of certain other PIDs, this invention uses the electrometer supplied in the gas chromatograph, normally installed for operating a flame ionization detector, which is a very common detector available from all major chromatograph manufacturers. The novel features of this invention relate to the unique design elements of the detector and to the use of a "lamp saver" circuit located in the lamp power supply module.

Figure 3:
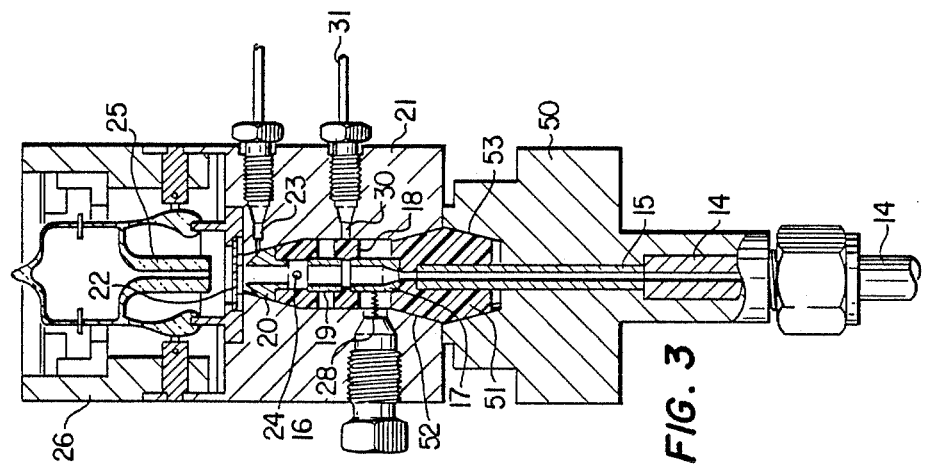
FIG. 3 is a cross-sectional view, taken through lines 3—3 of FIG. 2, of the photoionization detector of the present invention.

FIGS. 2 and 3 show cross sectional view of the detector. With reference to FIG. 2, the detector 13 is interfaced to the gas chromatograph column at 14. The sample stream is directed from the detector inlet through the glass-lined stainless steel transfer tube 15 and transfer port into the photoionization chamber 16 defined by the polarizing electrode 17, electrode spacer 18, collector electrode 19, ceramic insert 20, electrode biscuit 21, and lamp window 22. The transfer tube 15 rises through a mounting block 50 into the electrode biscuit 21 through a tapered seal 51. The tapered seal has two tapered surfaces 52, 53 which pilot against matched tapered openings in the electrode biscuit and mounting block. The seal also accepts the polarizing electrode 17 in a recess 55.

With reference to FIG. 3, the sample stream, is fluidically switched away from lamp window 22 by a sweep gas entering the photoionization chamber at sweep gas inlet port 23 and exits the chamber through exit transfer 24.

Ions created from exposure of the sample within the ionization chamber 16 by UV lamp 25 contained within lamp biscuit 26 are accelerated by polarizing electrode 17 to collector electrode 19. Electrical connections to the electrometer input and polarizing voltage source (contained within the electrometer's circuitry) are made via spring-loaded connectors 27 and 28.

With reference again to FIG. 2, a novel design feature of the PID exit port 24, 29 is that it forms the female portion of a tube connection, which enables the reactor of an electrolytic conductivity detector to be directly interfaced to the PID without the use of a transfer tube as required by conventional designs. The electrode biscuit contains a vent exit port 30 connected to a solenoid controlled vent valve (not shown) via the vent exit tube 31, which allows unwanted sample components to be vented from the detector photoionization chamber 16 prior to the exit port 29 and entering the ELCD reactor when installed.

The incorporation of a venting mechanism into the PID is an additional novel feature of this invention not found in any other PID. This feature when combined with the sweep gas feature, using an ELCD reaction gas as the sweep gas (i.e. hydrogen or air, depending upon ELCD mode of operation) enables the PID to provide the venting and reaction gas introduction functions of the ELCD, normally performed by the detector base of the ELCD, in addition to the normal photoionization function of the PID This allows the ELCD reactor to be interfaced directly to the PID, eliminating the need for ELCD detector base and the use of any transfer tubing to interface the two detectors. In this manner an unitized PID-ELCD detector system is formed, which requires the use of only one detector port.

Figure 4:
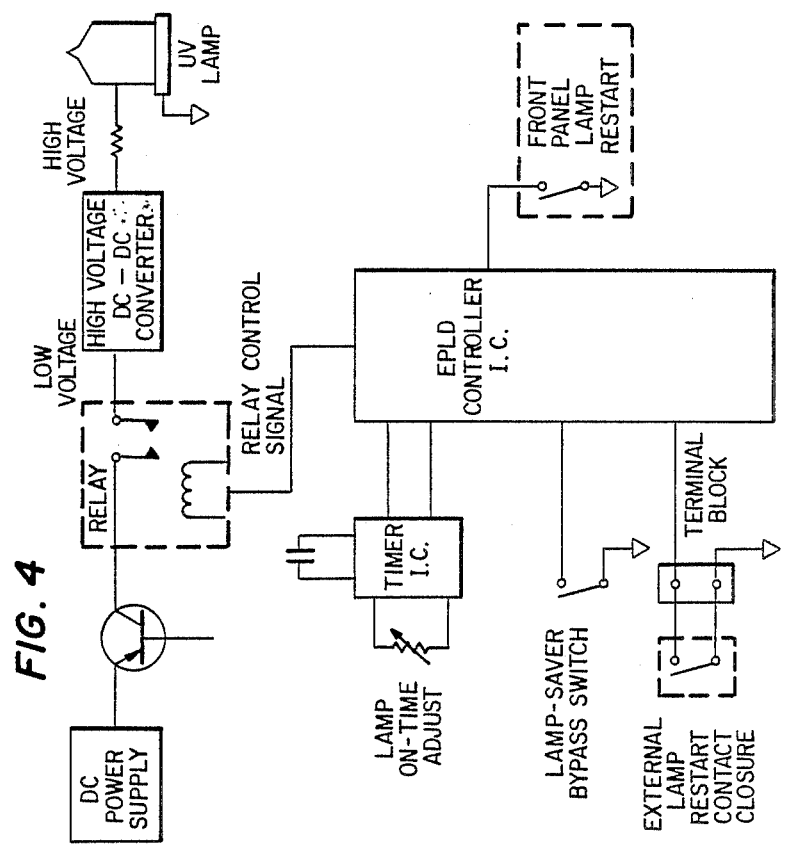
FIG. 4 is a schematic diagram of the lamp voltage control feature of the present invention.

The "lamp saver" feature of the PID lamp supply is an additional novel feature of this invention. The operation of this feature can be understood with the aid of the simplified circuit schematic shown in FIG. 4. Power to the UV lamp is automatically removed after a user-selectable time has elapsed unless the timer is reset by a contact closure activated by a pushbutton on the supply module or a contact closure resident on and activated by another instrument such as a gas chromatograph or a purge-and-trap sample concentrator. In this manner, power to the UV lamp will remain on during the entire time the detector is in use as long as the timer is set to a time longer than the chromatograph analysis time, because a ready signal (contact closure) will be generated by the chromatograph (or ancillary instrument) when it has completed a run and is ready to begin another. If not desired, the feature can be disabled by the "lamp saver" bypass switch.

The "lamp saver" feature is not found on any other PID, and for this reason is a novel feature of this invention. This feature is useful in the operation of the PID, because many of the UV lamps used have a fairly short life of approximately 500 to 600 hours. As a result, if one forgets to turn off the PID lamp supply and it is left on at night or for a weekend, a considerable portion of the lamp's life will be wasted.

The performance of the invention is shown in FIG. 5. Response of the PID to a mixture of aromatic and chlorinated hydrocarbon compounds pertinent to United States Environmental Protection Agency methods 601 and 602 is shown in this FIG. 5(a). The response of an ELCD connected in series and functioning with the PID as an unitized detector system is shown in FIG. 5(b). The excellent response of the ELCD shows that no loss in peak integrity occurs by passing the sample through the PID. Thus these novel design features can be seen to constitute definite analytical advantages. While we have described above the principles of the invention in terms of specific equipment and methods, it is to be understood that this description is made only by way of example and not as a limitation to be scope of the invention as set forth in the accompanying claims.

What is claimed is:

1. In a photoionization detector having an ultra-violet lamp and lamp window, the improvement comprising:
a photoionization chamber;
the chamber having a cylindrical polarizing electrode disposed therein, and a cylindrical collector electrode between the polarizing electrode and the lamp window, the collector electrode co-axial to the polarizing electrode.

2. The detector of claim 1, wherein a vent exit is located between the electrodes.

3. The detector of claim 1, wherein:
the ultra-violet lamp cooperates with a lamp saver.

4. The detector of claim 2, wherein:
an exit transfer is located between the lamp window and the vent exit.

5. The detector of claim 4, wherein:
a sweep gas inlet port is located between the exit transfer and the lamp window.

6. In a photoionization detector having an ultra-violet lamp and lamp window, the improvement comprising:
a photoionization chamber;
the chamber having a polarizing electrode;
a collector electrode;
and a sweep gas inlet port located between the electrodes and the lamp window.

7. The photoionization detector of claim 6, wherein:
the ultra-violet lamp is operatively controlled by a lamp saver means for prolonging lamp life.

8. The detector of claim 6, wherein:
the chamber further comprises an exit transfer aperture, the sweep gas inlet port located between the exit transfer aperture and the lamp window.

9. The detector of claim 6, wherein:
the chamber further comprises an insert, the insert having a central bore, the insert located between the lamp window and the electrodes, the insert adapted to direct the flow of sweep gas into proximity with the lamp window.

10. In a gas chromatography apparatus having a photoionization detector and another detector, the improvement comprising:
a photoionization detector having a lamp window and a photoionization chamber, the chamber having a sweep gas inlet port and a flow of sweep gas;
the sweep gas adapted to inhibit contact of a sample analyte with the lamp window.

11. The apparatus of claim 10, wherein:
the photoionization detector further comprises an exit transfer port;
the exit transfer port adapted to receive another detector;
the detector adapted to a flow of sweep gas from the sweep gas inlet port, through the exit transfer port.

12. The apparatus of claim 11, wherein:
the photoionization detector further comprises a threaded female aperture;
the threaded aperture forming an extension of the exit transfer port, the aperture adapted to receive a male threaded portion of a reactor.

13. The apparatus of claim 12, wherein:
the photoionization detector further comprises an insert within the chamber, the insert having a central bore, the exterior surface of the insert located adjacent the sweep gas inlet port.

14. An improved method of gas chromatography, wherein:
analyte gases are introduced into a photoionization chamber, the chamber having an inlet, an exit and a vent;
analyte gases are removed from the photoionization chamber, through the vent.

15. The method of claim 14, wherein
after selected analyte gases are vented, the vent is closed, and;
further removal of analyte gases, from the chamber, occurs through the exit.

16. The method of claim 14, wherein:
sweep gas is introduced into the chamber, and;
sweep gas and analyte gases are removed from the chamber, through the vent.

17. In a photoionization detector having a source of ionizing radiation and a window to such source and wherein sample gases are ionized within a photoionization chamber, the chamber having a sample intake and a sample exit, the improvement comprising:
a vent, the vent located between the sample intake and sample exit of the chamber, the vent adapted to route the flow of gas in the chamber away from the sample exit and the window.

18. The detector of claim 17, wherein:
the chamber further comprises a sweep gas inlet, the inlet adjacent the window.

19. In a method for gas chromatograph utilizing a photoionization detector, comprising a detector having an exit port and a lamp window which is exposed to the chamber of the detector, the improvement comprising
introducing a sweep gas into the chamber between the exit port and the lamp window, and;
removing the sweep gas from the chamber so as to inhibit contact of analyte with the lamp window.

20. The method of claim 19, wherein:
the method of chromatography further comprises a second analytical instrument;
the sweep gas is introduced from the photoionization detector into the second instrument and;
the sweep gas is utilized as a necessary reagent by the second instrument.

21. The method of claim 20, wherein:
the second instrument is the reactor of an electrolyte conductivity detector.

22. In a photoionization detector, the improvement comprising:
a mounting block having a tapered opening;
an electrode biscuit having a tapered opening; and
a tapered seal having two tapered surfaces, the seal adapted to engage both the electrode biscuit and mounting block, lying partially within each tapered opening.

23. The detector of claim 22, wherein:
the seal further comprises a recess adapted to receive an electrode.

24. The detector of claim 23, wherein:
the seal further comprises a central bore, the bore providing a clearance for a transfer tube.

* * * * *